(12) United States Patent
Adair

(10) Patent No.: US 10,842,195 B2
(45) Date of Patent: Nov. 24, 2020

(54) AEROSOL GENERATING DEVICE

(71) Applicant: JT International S.A., Geneva (CH)

(72) Inventor: Kyle Adair, Lisburn (GB)

(73) Assignee: JT International S.A. (CH)

( * ) Notice: Subject to any disclaimer, the term of this patent is extended or adjusted under 35 U.S.C. 154(b) by 0 days.

(21) Appl. No.: 15/522,658

(22) PCT Filed: Oct. 27, 2015

(86) PCT No.: PCT/EP2015/074856
§ 371 (c)(1),
(2) Date: Apr. 27, 2017

(87) PCT Pub. No.: WO2016/066635
PCT Pub. Date: May 6, 2016

(65) Prior Publication Data
US 2017/0318860 A1    Nov. 9, 2017

(30) Foreign Application Priority Data

Oct. 29, 2014  (EP) ..................... 14190889

(51) Int. Cl.
*A24F 47/00* (2020.01)
*A61M 15/06* (2006.01)
*A61M 11/04* (2006.01)
*A61M 16/00* (2006.01)
*A61M 15/00* (2006.01)

(52) U.S. Cl.
CPC ......... *A24F 47/008* (2013.01); *A61M 11/042* (2014.02); *A61M 15/06* (2013.01); *A61M 15/00* (2013.01); *A61M 2016/0018* (2013.01); *A61M 2016/0021* (2013.01); *A61M 2016/0039* (2013.01); *A61M 2205/276* (2013.01); *A61M 2205/3368* (2013.01); *A61M 2205/3375* (2013.01); *A61M 2205/3653* (2013.01); *A61M 2205/8206* (2013.01)

(58) Field of Classification Search
CPC ....................................... A24F 40/49
See application file for complete search history.

(56) References Cited

U.S. PATENT DOCUMENTS

| 2012/0186594 A1 | 7/2012 | Liu |
| 2013/0160764 A1 | 6/2013 | Liu |
| 2013/0319989 A1 | 12/2013 | Liu |

(Continued)

FOREIGN PATENT DOCUMENTS

| CN | 103827650 A | 5/2014 |
| CN | 103917119 A | 7/2014 |

(Continued)

OTHER PUBLICATIONS

Taiwanese Office Action for Application No. 104135503, dated Mar. 3, 2017 (17 Pages).

(Continued)

*Primary Examiner* — Michael H. Wilson
*Assistant Examiner* — Katherine A Will
(74) *Attorney, Agent, or Firm* — Lerner, David, Littenberg, Krumholz & Mentlik, LLP

(57) ABSTRACT

An aerosol generating device, in particular an electronic cigarette or a vaporizer, has means to avoid children or young persons to use said aerosol generating device.

17 Claims, 1 Drawing Sheet

(56) References Cited

U.S. PATENT DOCUMENTS

2014/0202472 A1 7/2014 Levitz et al.
2017/0135400 A1* 5/2017 Liu ..................... A24F 47/008

FOREIGN PATENT DOCUMENTS

| DE | 10 2010 012600 A1 | 9/2010 |
|---|---|---|
| JP | 2013526834 A | 6/2013 |
| WO | 2013/083635 A1 | 6/2013 |

OTHER PUBLICATIONS

International Search Report and Written Opinion for Application No. PCT/EP2015/074856, dated Jan. 25, 2016 (10 pages).

* cited by examiner

AEROSOL GENERATING DEVICE

Priority is claimed under 35 U.S.C. § 119 to European Application No. 14190889.7 filed on Oct. 29, 2014 and under 35 U.S.C. § 365 to PCT/EP2015/074856 filed on Oct. 27, 2015.

FIELD OF THE INVENTION

The present invention pertains to an aerosol generating device, in particular electronic cigarettes or vaporizers which comprises means to avoid children or young person to use said aerosol generating device.

BACKGROUND

Electrically operated cigarettes, so-called "e-cigarettes", usually include an aerosol generator including a heater powered by an electrical power source and a liquid reservoir containing flavoured or unflavoured liquids that can be volatilized using the heater and transferred to a user of the e-cigarette in an airflow through a mouthpiece of the e-cigarette. Such an electrically operated cigarette is for example known from the document US 2013/0160764 A1.

E-cigarettes may employ biologically and/or physiologically active substances comprised in the liquids which need to be handled with specific care and caution. To protect from harm due to improper handling of e-cigarettes it would be desirable to develop e-cigarettes with inherent childproofing means.

SUMMARY OF THE INVENTION

According to an idea the present invention there is provided an aerosol generating device comprising: a housing having at least one air inlet and at least one air outlet and defining a principal air flow channel there between; an aerosol generator positioned within the housing for providing an aerosol to the outlet; an activation device positioned in the principal air flow channel and arranged to selectively activate the aerosol generator; and air flow modifying means arranged enable a user to modify the airflow in the principal airflow in use, said modified airflow being detected by the activation device and thereby activating the aerosol generator.

With an aerosol generating device according to the invention, tampering of the aerosol generating device by children may be prevented or at least impeded, thus safeguarding the children's health and wellbeing.

According to an embodiment of the aerosol generating device, the aerosol generating device may further comprise a power source configured to supply the aerosol generator with electrical energy. In a specific embodiment, the aerosol generator may further comprise a heating element coupled to the power source via the switch.

The activation device may permit the aerosol generator to generate an aerosol when the air flow rate value in the principal airflow channel is in a pre-determined range or have reach a pre-determined threshold.

According to an embodiment the airflow modifying means are located in the aerosol generating device, upstream in the principal airflow channel to the activation device.

The airflow modifying means may be provided by a further airflow channel distinct from, but in fluid engagement with, the principal airflow channel.

The aerosol generating device may be formed from two separable parts and the modifying means are located on one of said parts.

The modifying means may modulate the air flow rate in the principal airflow channel by selectively increasing or decreasing it. In such a case said airflow modifying means may modulate the air flow rate value in the principal airflow channel with airflow bypass means to prevent the air flow in the principal channel from exceeding a pre-determined range until activated by a user.

Said modifying means may comprise at least one of holes or airflow inlets in the outer part of the device or others similar means in such a case, the modifying means may be deactivated by a user by manual blocking by at least one finger. The airflow modifying means may be also electronically or mechanically deactivated.

The activation device may comprise at least one airflow sensor, which may be one of a mechanical-to-electrical sensor, a micro-electromechanical systems (MEMS) activation sensor, a pressure differential sensor, a mass flow sensor, a fluid velocity sensor, or a flow rate sensor. Alternatively the least one airflow sensor may be a microphone, such as a dynamic microphone, a condenser microphone, a capacitance microphone or piezoelectric microphone.

The action of the airflow modifying means may for example be effected manually, i.e. by the user placing his fingers or other parts of his hand over holes or airflow inlets in a bypass airflow channel in the aerosol generating device in order to prevent air streaming into the bypass airflow channel upon inhaling air through a mouthpiece of the aerosol generating device. It may also be possible to provide one or more blocking actuators which trigger a mechanical blocking mechanism that is operated indirectly by the user, for example by pushing a button to activate an electrically driven blocking unit or by manually operating a slider, shutter or valve to indirectly realize a blocking action of a bypass airflow channel.

The holes or inlets of any bypass airflow channel in the aerosol generating device, or the blocking actuators, as applicable, may be placed or arranged strategically around the outer circumference of a housing of the aerosol generating device so that some degree of knowledge, precision and/or accuracy is necessary to achieve the desired blocking effect for the bypass airflow channel. Thus, the manner of activating the aerosol generation mechanism will be obfuscated to unintended use—the aerosol generation mechanism will particularly not be activated upon an inhaling action at the mouthpiece of the aerosol generating device alone.

The embodiments of aerosol generating devices as disclosed herein are child- and tamperproof, specifically due the protection mechanisms against uncontrolled or unsolicited access.

BRIEF DESCRIPTION OF THE DRAWINGS

The invention will be explained in greater detail with reference to exemplary embodiments depicted in the drawings in which.

DETAILED DESCRIPTION OF EMBODIMENTS

Although specific embodiments have been illustrated and described herein, it will be appreciated by those of ordinary skill in the art that a variety of alternate and/or equivalent implementations may be substituted for the specific embodiments shown and described without departing from the scope of the present invention.

Generally, this application is intended to cover any adaptations or variations of the specific embodiments discussed herein. In the present invention, reference is made to aerosol generators. Such aerosol generators or aerosol generating devices are generally intended to comprise any apparatus capable of converting electric energy and/or combustion energy into heat and subsequently heating and thereby volatilizing particles in a vaporisable material, for example, a liquid or gaseous composition contained within a part of the aerosol generating device. Aerosol generating devices within the meaning of the present invention may transport the volatilized particles in an airflow through the aerosol generating device to a user of the device, the user of the device being able to activate or deactivate the generation of aerosol and to control the duration, velocity and volume of the airflow by means of puffing or inhaling action.

In respect of the childproofing aspects of the invention it will also be appreciated that these may be supplemented by additional features to add further childproofing, such as further activation switches, flaps or other mechanical, electrical or electronic features.

Figure 1:
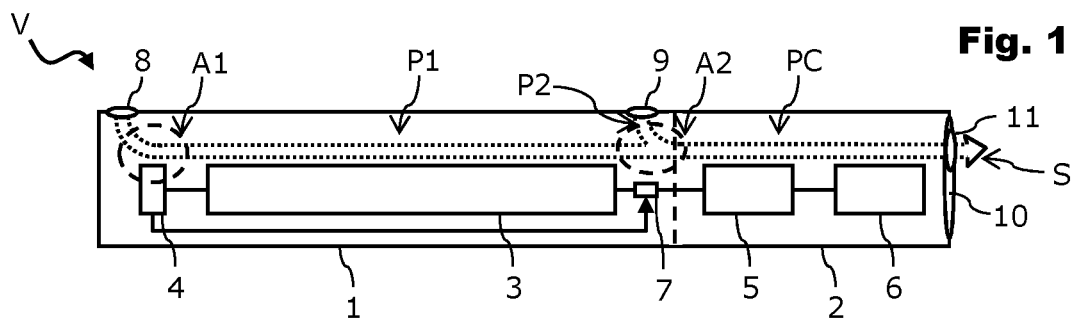
FIG. 1 schematically illustrates a functional depiction of an aerosol generating device according to an embodiment of the invention.

FIG. 1 schematically illustrates a functional depiction of an aerosol generating device V. The aerosol generating device V may generally comprise a housing. The housing may be formed as integral hollow body. It may also be possible for the housing to have a battery housing section 1 and a vaporising housing section 2, such as the ones exemplarily depicted in FIG. 1, which together form a generally hollow body of the aerosol generating device V and are fluidly connected to each other.

The battery housing section 1 may house a power source 3, such as an electrical power source, for example a battery or an accumulator. The battery housing section 1 may also comprise an activation device in the form of sensor system 4 that is configured to selectively activate a switch 7 between the power source 3 and components of the vaporising housing section 2. The battery housing section 1 and the vaporising housing section 2 may together form a substantially cylindrical device body of the aerosol generating device V. However, it should be appreciated that any other outer shape, for example prismatic or ellipsoid shapes may be suitable for the battery housing section 1 and the vaporising housing section 2 as well.

The vaporising housing section 2 comprises a vaporising mechanism, which may for example comprise an aerosol generator and a mouthpiece as separate components. The aerosol generator may for example comprise a heating element 5 electrically connected to the power source 3, a liquid storage component 6, and a means for providing a liquid interface between the heating element 5 and liquid storage component 6 such as a wick. The vaporising housing section 2 may also comprise a cartomizer, i.e. an integral combination of an atomizer and a liquid storage component embedded in a hollow housing, the end of it forming a mouthpiece 10 having an airflow outlet 11.

As an exemplary configuration, FIG. 1 depicts a vaporising housing section 2 comprising a heating element 5, for example a nichrome wire coil, which is coupled to the power source 3 via the switch 7. The heating element 5 is supplied with energy for its operation by the power source 3 when the switch 7 is closed. FIG. 1 further exemplarily depicts a liquid storage component 6 fluidly coupled to the heating element 5 in operative connection so that the heating element 5 may supply heating energy to a liquid or gas contained with the liquid storage component 6, thereby causing certain compounds contained in the liquid to volatilize into an airflow S streaming through the vaporising housing section 2. The vaporising housing section 2 may have a mouthpiece with an airflow outlet, generally depicted as reference numeral 11, through which aerosol S generated from the liquid storage component 6 may be guided towards a user of the aerosol generating device V performing an inhaling action at the mouthpiece 10.

The liquid storage component 2 may comprise a liquid reservoir in which a liquid composition with compounds to be volatilized may be contained or a sponge wetted with such a liquid. The liquid storage component 6 may be in connection by means of a liquid interface with the heating element 5 which may convey heating energy to the liquid, thereby evaporating or volatilizing certain compounds of the liquid. The liquid interface between the heating element 5 and the liquid storage component 6 may result from the heating element 5 forming an electrode plunged into the liquid reservoir or, in a more common alternative, from a liquid transfer arrangement such as a wick extending between the liquid storage component 6 and the heating element 5.

The air stream or airflow S to be inhaled by the user of the aerosol generating device V may flow through a common airflow channel section PC extending through the liquid storage component 6 or around it. Thereby, upon an air drawing action of the user at the mouthpiece 10 an aerosol is generated in the aerosol generating device due to the low pressure created by puffing at the mouthpiece 10 and the aerosol can be inhaled by the user from the airflow outlet 11 at the mouthpiece 10.

The aerosol generating device V may further comprise electronic circuitry controlling the operation of the aerosol generating device V and/or various buttons or light emitting elements on its outer surface, all of which are not shown in FIG. 1 for purposes of improved clarity of the drawings.

The battery housing section 1 and the vaporising housing section 2 may be separable, for example by means of a connector that is arranged in the vaporising housing section 2 in order to mechanically and realisably connect the vaporising housing section 2 to the battery housing section 1. The connector and the connector receptacle of the sections 1 and 2 may be constructed in a complementary and corresponding manner, for example by a moulding procedure, to realize complementary snap-fit parts or interlocking clearances. For example, the connector may include protrusions that interlock with recesses in the connector receptacle when edging the connector into the connector receptacle. Moreover, the connector and the connector receptacle may be designed with electrical connections being formed between the power source 3 and the heating element 5 upon connecting the battery housing section 1 and the vaporising housing section 2.

It may further be possible to provide sealing means, such as a rubber O-ring or similar, between the connector and the connector receptacles in order to fluidly seal the interface between the battery housing section 1 and the vaporising housing section 2 against the environment.

With respect to FIG. 1, the function of the aerosol generating device V will now be described in further detail. The aerosol generating device V comprises one or more airflow inlets or holes 8 within its outer body. For example, at the opposite end of the mouthpiece 10, one or more holes 8 may be formed in the battery housing section 1, thereby creating a principal air flow channel which acts as an activation airflow channel P1 between the tip of the battery housing section 1 and a branching airflow junction A2 within the device body. This principal airflow channel P1 is used for generating an aerosol at the heating element 5 when air is drawn through the first airflow intakes 8 from the mouthpiece 10 by a user as previously described.

On the other hand, the aerosol generating device may comprise one or more bypass airflow inlets or holes 9 being formed in the body of the aerosol generating device V. The bypass airflow inlets 9 allow air to stream into the aerosol generating device V along a bypass airflow channel P2. The principal airflow channel P1 and the bypass airflow channel P2 branch off at the branching airflow junction A2 within the device body, the aerosol generating device V extending through the mouthpiece 10 to convey air and vaporized particles of liquids forming an aerosol to a user. The bypass airflow channel P2 forms a bypass for air bypassing the principal airflow channel P1 as will be described below.

Air being drawn in by a user in the airstream S through an inhaling action at the mouthpiece 10 will flow at a total volumetric flow rate that is the sum of the volumetric flow rates through the separate airflow channels P1 and P2. Given a constant total volumetric flow rate in the airstream S at the mouthpiece 10 and without any active blocking action of the one or more bypass airflow inlets 9, the volumetric flow rate through the bypass airflow channel P2 will be non-zero, thus decreasing the remaining volumetric flow rate through the principal airflow channel P1 by that amount.

The activation device 4 is configured to detect a variation of at least one airflow parameter such as pressure, velocity, airflow rate, at a location within the body of the aerosol generating device V generally denoted air flow sensing location A1 indicated by a dotted circle which location is near the active sensor surface. For example, the activation device 4 may comprise a mechanical-to-electrical transducer that is able to produce an electrical signal depending on detected variations in air pressure in its vicinity. The activation device 4 may alternatively, for example, comprise a microphone, such as a dynamic microphone, condenser microphone, capacitance microphone or piezoelectric microphone. It may also be possible to employ microelectromechanical systems (MEMS) activation sensors. Alternatively, other types of activation sensors may also be used such as pressure differential sensors, mass flow sensors, velocity sensors, flow rate sensors, temperature sensors or the like. It may also be possible to employ multiple types of sensors in the activation sensor and to combine their measurement values to a consolidated detection result which may then be compared to a combined activation threshold or a pre-determined range.

The activation device 4 may have an activation threshold or be activated in a pre-determined range value (or combined activation threshold for multiple sensors) for selectively activating a switch 7 between the power source 3 and the heating element 5. Other ways to activate the heating element could be contemplated and accessible to the one skilled in the art. When the vacuum pressure, i.e. the drop in pressure in the region A1 in the vicinity of the active sensor surface of the activation sensor 4 surpasses the activation threshold or the pre-determined range value, the activation sensor 4 will close the switch 7, thereby establishing an electrical connection between the power source 3 and the heating element 5 and allowing the heating element 5 to be powered by the power source 3.

In its zero position, i.e. without any external influence, the second airflow inlets 9 will be open allowing air to flow through the bypass airflow channel P2. This in turn will keep the drop in pressure created by an inhaling action of a user in the principal airflow channel P1 low enough not to set off the activation device 4 to close the switch 7. For example, average volumetric flow rates associated with a puff or draw of an adult human are between 18 and 20 ml/s, with peak flow rates of up to 60 ml/s. The sizing and number of second airflow inlets 9 as well as the dimensions of the bypass airflow channel P2 may therefore be designed in such a way that the fraction of air being drawn in through the bypass airflow channel P2 in relation to the overall airflow in the principal channel section P1 is sufficiently high to not trip or enable the activation device 4 when the second airflow intakes 9 are not actively blocked. For example, minimum threshold flow rates for the activation sensor system 4 may be about 10 ml/s. Unintended drawing at the mouthpiece 10 will not be able to activate the vaporization mechanism since the second airflow intakes 9 are not blocked.

During intended use of an adult user of the aerosol generating device V, the user will need to block the second airflow inlets 9 to reduce the fraction of airflow streaming through the bypass airflow channel P2 to zero or near zero while at the same time inhaling through the mouthpiece 10. The volumetric flow rate through the region A1 will correspondingly increase and the drop in pressure near the activation device 4 will surpass the threshold or the pre-determined rate value to close the switch 7 and activate the vaporization mechanism of the aerosol generating device V.

Figure 2:
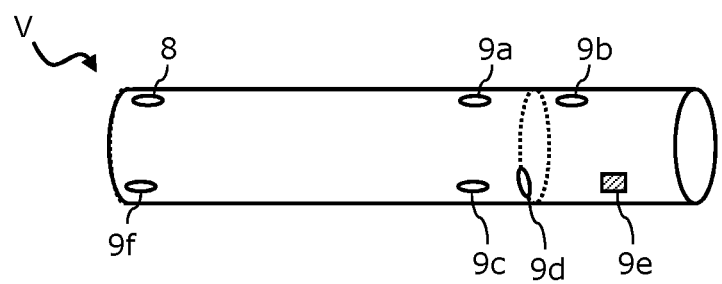
FIG. 2 schematically illustrates an outer view of an aerosol generating device according to further embodiments of the invention.

FIG. 2 depicts possible locations and types of second airflow inlets 9, indicated with reference numerals 9*a*, 9*b*, 9*c*, 9*d*, 9*f*. It is to be noted that the illustration of FIG. 2 is merely exemplary, and that actual aerosol generating devices V may employ only one or a few of the possible locations and types of second airflow inlets separately or in combination, depending on the type, geometry and size of the aerosol generating device to enable the creation of one or more bypass airflow channels The aerosol generating device V may comprise second airflow inlets as holes 9*a* in the battery housing section 1 or as holes 9*b* in the vaporising housing section 2. The holes may be formed at different positions around the circumference of the battery housing section 1 or the vaporising housing section 2 (indicated exemplarily with hole 9*c*). It may also be possible to provide for gaps 9*d* in the connection between the battery housing section 1 and the vaporising housing section 2, for example by creating cut-outs or notches in the mechanical connectors of the respective section.

Figure 3:
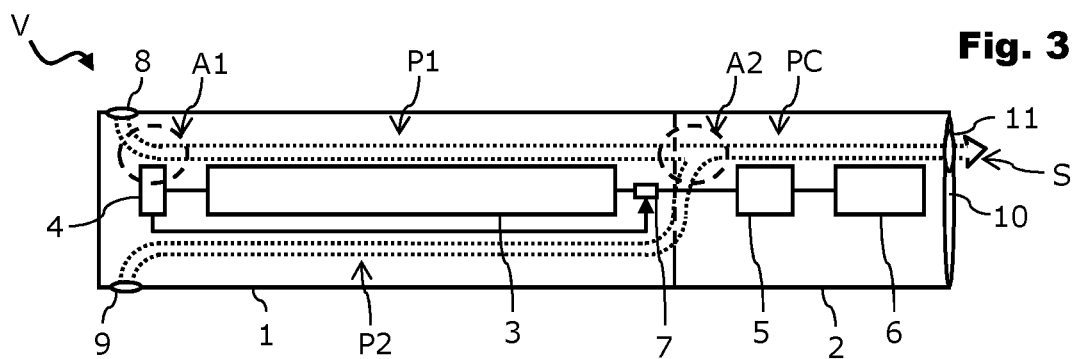
FIG. 3 schematically illustrates a functional depiction of an aerosol generating device according to yet another embodiment of the invention.

The second airflow inlets may also be formed as holes 9*f* near the rear end of the battery housing section 1 far from the mouthpiece 10. An example of an aerosol generating device V with such holes 9*f* as second airflow inlets 9 is illustrated in FIG. 3.

Finally, it may also be possible to provide for indirect closing means to initiate a blocking action of the second airflow inlets 9. For example, a blocking actuator 9*e* may be formed as a button, a slider, a shutter, a valve or similar means to trigger a mechanical blocking mechanism to shut off the second airflow inlets 9. The mechanical blocking mechanism may be spring-loaded so that the blocking actuator 9e will have to be actively held down in order to keep the second airflow inlets 9 blocked during inhalation. Alternatively, it may be possible to provide for a passive closing mechanism such as a ring or any other means for continuously closing the second airflow inlets 9 during the time the aerosol generating device V is intended for use so that it can be avoided for the user to maintain the position of his/her fingers on the device or misplacement of the fingers by the user. This passive closing mechanism may be tripped initially at the beginning of the intended usage and deactivated again once the usage is to be ended.

The number, placement on the aerosol generating device V and dimension of the different holes 9a, 9b, 9c, 9d, 9f and blocking actuators 9e may vary and may be selected depending on the type of components in the aerosol generating device V. For example, the holes 9a, 9b, 9c, 9d, 9f may be circular holes having a diameter between 0.1 mm and 2 mm.

With the aerosol generating devices as illustrated herein, it is possible to implement an easy and fairly inexpensive childproofing solution for e-cigarettes which should be able to pass regulatory tests under the Tobacco Products Directive. As a side effect, the airflow inlets on the outside of the device body of the aerosol generating device may be arranged with ulterior motives regarding aesthetics, design and appearance in mind. Decoratively arranged airflow intakes which at the same time provide for the necessary child-resistance may be a useful selling point.

In the foregoing detailed description, various features are grouped together in one or more examples or examples with the purpose of streamlining the disclosure. It is to be understood that the above description is intended to be illustrative, and not restrictive. It is intended to cover all alternatives, modifications and equivalents. Many other examples will be apparent to one skilled in the art upon reviewing the above specification.

The invention claimed is:

1. An aerosol generating device comprising:
   a housing having at least one air inlet and at least one air outlet and defining a principal airflow channel therebetween;
   an aerosol generator positioned within the housing and configured to provide an aerosol to the outlet;
   an activation device configured to measure an airflow in the principal airflow channel and arranged to selectively activate the aerosol generator in order to permit the aerosol generator to generate the aerosol, wherein the aerosol generator is activated when an airflow rate value in the principal airflow channel is in a predetermined range or has reached a predetermined threshold; and
   airflow modifying means arranged to enable a user to modify the airflow in the principal airflow channel in use, the airflow modifying means provided by a bypass channel that is distinct from, but in fluid engagement with, the principal airflow channel,
   wherein the aerosol generating device has a smoking state and a childproofing state,
   the aerosol generating device in the smoking state having the bypass channel blocked and the aerosol generator activated such that the airflow at the at least one air outlet contains the aerosol,
   the aerosol generating device in the childproofing state having the bypass channel unblocked and the aerosol generator deactivated such that the airflow at the at least one air outlet does not contain the aerosol, and the aerosol generating device being configured to automatically switch between the smoking state and the childproofing state in response to blocking or unblocking of the bypass channel.

2. The aerosol generating device of claim 1, wherein the airflow modifying means is located upstream in the principal airflow channel to the activation device.

3. The aerosol generating device of claim 1, wherein the aerosol generator is selectively activated or selectively deactivated by the user respectively substantially blocking or unblocking a bypass airflow through the bypass channel, which causes the user-controlled modification of the airflow rate value in the principal airflow channel.

4. The aerosol generating device of claim 1, wherein the aerosol generating device is formed from two separable parts and the modifying means is located on one of said parts.

5. The aerosol generating device of claim 1, wherein the modifying means modulates the air flow rate in the principal airflow channel by selectively increasing or decreasing it.

6. The aerosol generating device of claim 1, wherein said airflow modifying means is configured to modulate the airflow rate value in the principal airflow channel with airflow bypass means configured to prevent the airflow in the principal airflow channel from exceeding a pre-determined range until the airflow modifying means is activated by a user.

7. The aerosol generating device of claim 1, wherein said airflow modifying means comprises at least one of holes or airflow inlets in an outer part of the device.

8. The aerosol generating device of claim 1, wherein the airflow modifying means can be electronically deactivated.

9. The aerosol generating device of claim 1, further comprising a power supply and wherein the activation device comprises a switch configured to regulate the delivery of power from the power supply to the aerosol generator.

10. The aerosol generating device of claim 1, wherein the activation device is configured to permit the aerosol generator to generate an aerosol when the airflow rate value in the principal airflow channel is in a pre-determined range.

11. The aerosol generating device of claim 1, wherein the activation device comprises at least one airflow sensor.

12. The aerosol generating device of claim 11, wherein the at least one airflow sensor is one of a mechanical-to-electrical sensor, a micro-electromechanical systems (MEMS) activation sensor, a pressure differential sensor, a mass flow sensor, a fluid velocity sensor, or a flow rate sensor.

13. The aerosol generating device of claim 11, wherein the at least one airflow sensor is a microphone.

14. The aerosol generating device of claim 7, wherein the airflow modifying means is activated by a user by manual blocking by at least one finger.

15. An aerosol generating device comprising:
   a housing;
   at least one airflow outlet;
   at least one air inlet formed in the housing;
   at least one further airflow inlet distinct from said at least one air inlet formed in the housing;
   a principal airflow channel between the at least one airflow outlet and the at least one airflow inlet and in fluid connection with a branching junction within the housing;
   a bypass airflow channel between the at least one further airflow inlet and the branching junction, the bypass airflow channel being distinct from the principal airflow channel;

an aerosol generator comprising a vaporization mechanism configured to volatilize compounds of a liquid or gas from a storage component of the vaporization mechanism into an airflow streaming through the principal airflow channel;

a switch coupled to the vaporization mechanism and configured to activate the vaporization mechanism upon closing; and an activation device configured to measure at least one airflow parameter within the principal airflow channel and to selectively close the switch, if the at least one airflow parameter exceeds a predetermined activation threshold or a pre-determined range value, wherein the aerosol generating device has a smoking state and a childproofing state, the aerosol generating device in the smoking state having the bypass airflow channel blocked and the aerosol generator activated such that the airflow at the at least one air outlet contains the aerosol, the aerosol generating device in the childproofing state having the bypass airflow channel unblocked and the aerosol generator deactivated such that the airflow at the at least one air outlet does not contain the aerosol, and the aerosol generating device being configured to automatically switch between the smoking state and the childproofing state in response to blocking or unblocking of the bypass airflow channel.

16. The aerosol generating device of claim 1, wherein the airflow modifying means is configured to be mechanically deactivated.

17. The aerosol generating device of claim 13, wherein the microphone, is one of a dynamic microphone, a condenser microphone, a capacitance microphone or piezoelectric microphone.

* * * * *